(12) United States Patent
Apantaku

(10) Patent No.: US 11,135,114 B2
(45) Date of Patent: Oct. 5, 2021

(54) MEDICAL SHELF

(71) Applicant: Olubukola Apantaku, Red Deer (CA)

(72) Inventor: Olubukola Apantaku, Red Deer (CA)

(*) Notice: Subject to any disclaimer, the term of this patent is extended or adjusted under 35 U.S.C. 154(b) by 223 days.

(21) Appl. No.: 16/586,676

(22) Filed: Sep. 27, 2019

(65) Prior Publication Data
US 2021/0093501 A1 Apr. 1, 2021

(51) Int. Cl.
*A61G 13/10* (2006.01)
*A61G 13/00* (2006.01)

(52) U.S. Cl.
CPC ......... *A61G 13/10* (2013.01); *A61G 13/0009* (2013.01)

(58) Field of Classification Search
CPC .............................. A61G 13/10; A61G 13/009
See application file for complete search history.

(56) References Cited

U.S. PATENT DOCUMENTS

| 3,386,444 A * | 6/1968 | Brenner ............... A61G 13/102 604/357 |
| 4,011,944 A | 3/1977 | Cooley et al. |
| 4,229,420 A | 10/1980 | Smith et al. |
| 5,195,538 A | 3/1993 | Eldridge, Jr. et al. |
| 5,454,797 A | 10/1995 | Haswell |
| 5,490,975 A | 2/1996 | Dane |
| 5,511,674 A | 4/1996 | Boyd et al. |
| 5,944,014 A | 8/1999 | Webb |

FOREIGN PATENT DOCUMENTS

| CN | 2234250 | 9/1996 |
| CN | 203389046 U | 1/2014 |
| CN | 203677267 U | 7/2014 |
| CN | 203790045 U | 8/2014 |
| MX | 2009013769 A | 6/2011 |

* cited by examiner

*Primary Examiner* — Fredrick C Conley
(74) *Attorney, Agent, or Firm* — Argus Intellectual Enterprise; Jordan Sworen; Daniel Enea

(57) ABSTRACT

A medical shelf for holding surgical instruments in a convenient location during obstetric care. The medical shelf includes a tray having pair of arms extending from opposing ends of a rear side thereof, wherein the arms can mount to an end of a birth delivery bed. In a mounted position, the tray provides a surface that can receive surgical instruments to allow a medical professional the ability to conveniently access the instruments while performing a procedure on a patient positioned on the bed. A first brace secures each arm to the tray in a perpendicular position and a second brace secures each arm in an L-shaped configuration. A lip is disposed around a perimeter of the tray. A gap is disposed between the arms to allow the medical professional positioned on a front side of the tray to access the patient positioned on the opposing side of the tray.

19 Claims, 3 Drawing Sheets

MEDICAL SHELF

BACKGROUND OF THE INVENTION

The present invention relates to a medical shelf. More specifically, the present invention relates to a medical shelf having a tray for supporting surgical instruments and a pair of arms for mounting the tray to an end of a birth delivery bed.

Hospitals and other medical facilities utilize various bed types having a standard box-like shape for receiving patients and performing various medical procedures. However, for births and other types of vaginal procedures, a birth delivery bed is used in order to allow proper positioning of the patient and to provide for the medical professional to have the best access to the patient during the procedure. Birth delivery beds have a central U-shaped or semi-circular cutout to allow for the procedure to take place at the foot of the bed. Further, medical professionals require various surgical instruments when performing procedures, such as vaginal repairs. Unfortunately, in order to obtain a necessary instrument, the physician or midwife must turn away from the patient and reach in a different location to find the appropriate instrument. This increases the length of procedure time and can cause a brief loss of focus of the medical professional during the operation.

There have been attempts to provide more convenient access to surgical instruments, such as rolling trays. For example, the medical professional may utilize a rolling tray that is located behind or to the side. However, none of the known devices provide medical shelf that is mountable to a birth delivery bed and positioned between the medical professional and the patient seated in the birth delivery bed. Therefore, there exists a need for a medical shelf that allows a physician, midwife, or other medical professional to conveniently address perineal injuries or perform obstetric trauma treatment without having to continuously turn his or her back to the delivery table for the instruments needed.

In light of the devices disclosed in the known art, it is submitted that the present invention substantially diverges in design elements and methods from the known art and consequently it is clear that there is a need in the art for an improvement for a medical shelf. In this regard the instant invention substantially fulfills these needs.

SUMMARY OF THE INVENTION

In view of the foregoing disadvantages inherent in the known types of medical shelves now present in the known art, the present invention provides a new medical shelf wherein the same can be utilized for holding surgical instruments in a convenient location during obstetric care.

It is an objective of the present invention to provide a medical shelf comprising a tray having pair of L-shaped arms extending from opposing ends of a rear side of the tray. The arms are configured to mount to an end of a birth delivery bed. In some embodiments, a fastener is disposed on the arms to removably secure the arms to the delivery bed.

It is another object of the present invention to provide a medical shelf comprising a first brace configured to secure each arm to the tray in a perpendicular position and a second brace configured to secure each arm in an L-shaped configuration. In some embodiments, a lip is disposed around a perimeter of the tray.

It is yet another objective of the present invention to provide a medical shelf comprising a gap disposed between the pair of arms to allow the medical professional positioned on a front side of the tray to access the patient positioned on the opposing side of the tray.

It is therefore an object of the present invention to provide a new and improved medical shelf that has all of the advantages of the known art and none of the disadvantages.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
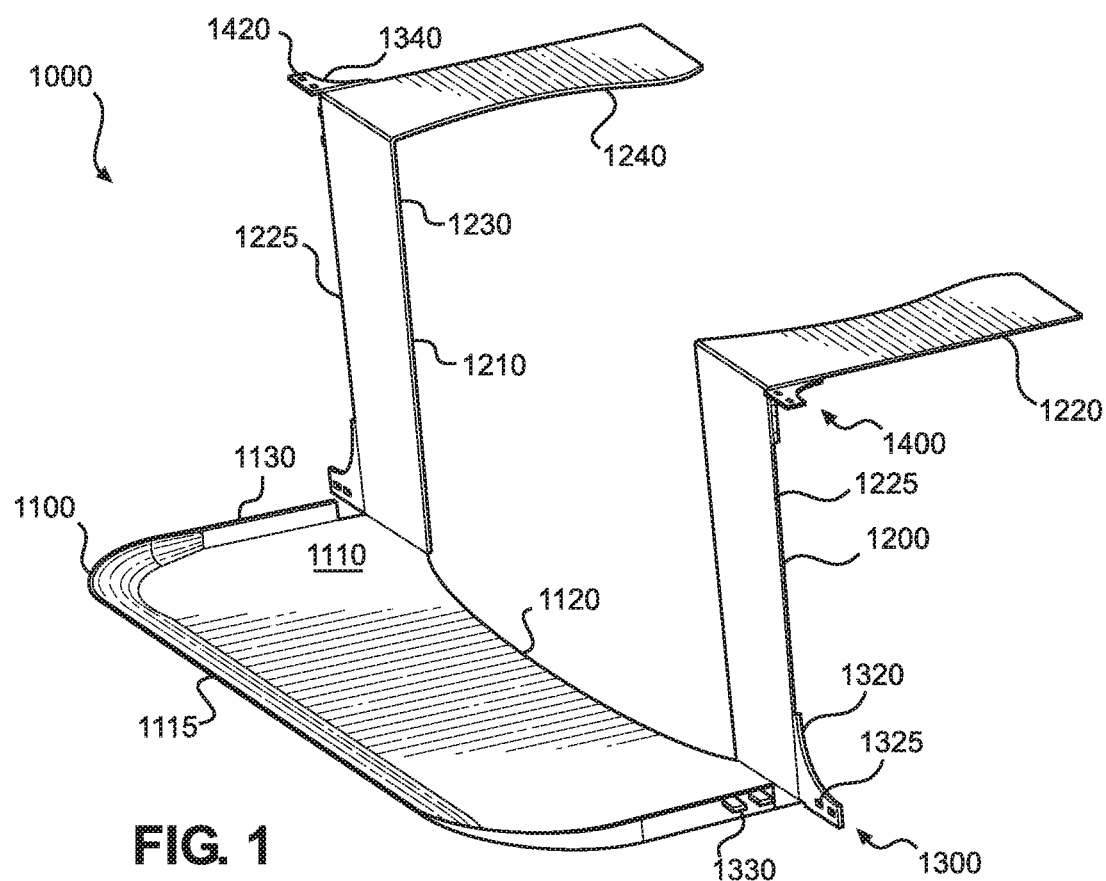
FIG. 1 shows a perspective view of an embodiment of the medical shelf, wherein the first and second brace are unsecured.

Reference is made herein to the attached drawings. Like reference numerals are used throughout the drawings to depict like or similar elements of the medical shelf. For the purposes of presenting a brief and clear description of the present invention, the preferred embodiment will be discussed as used for mounting to a birth delivery bed during a medical procedure. The figures are intended for representative purposes only and should not be considered to be limiting in any respect.

Figure 2:
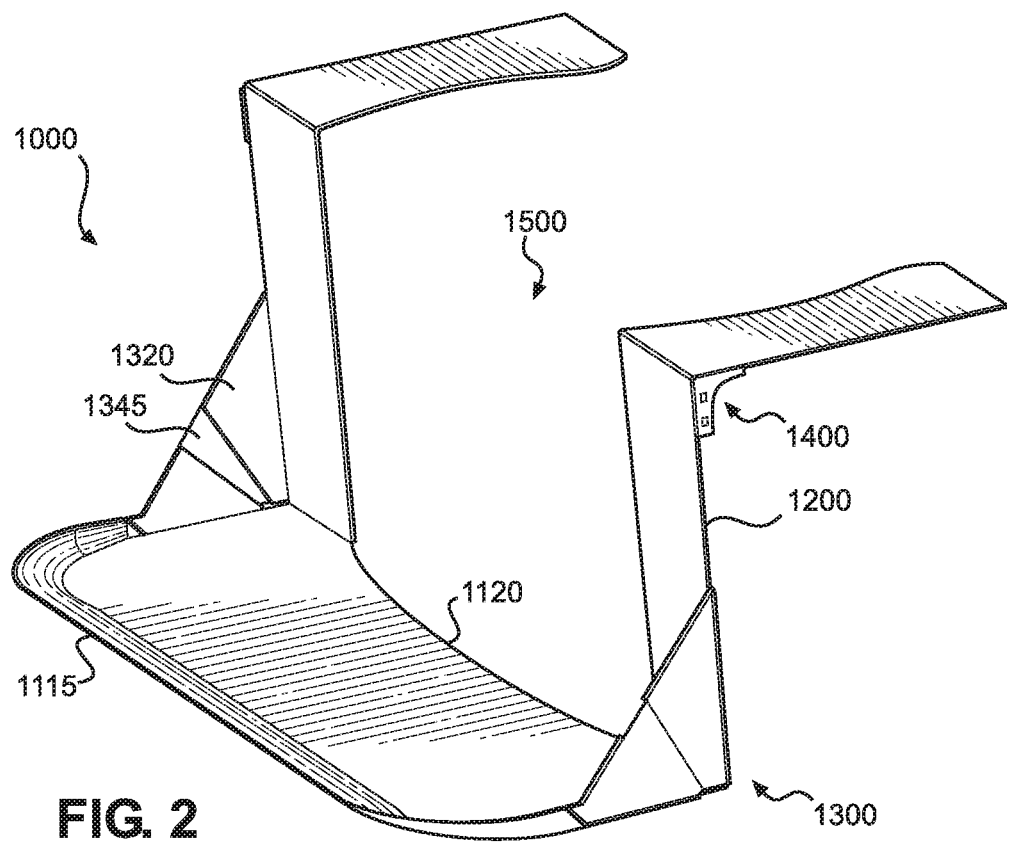
FIG. 2 shows a perspective view of an alternative embodiment of the medical shelf, wherein the first and second brace are secured.

Referring now to FIGS. 1 and 2, there is shown a perspective view of an embodiment of the medical shelf, wherein the first and second brace are unsecured and a perspective view of an alternative embodiment of the medical shelf, wherein the first and second brace are secured, respectively. The medical shelf 1000 includes a tray 1100 configured to receive and support surgical instruments thereon. In the illustrated embodiment, the tray 1100 comprises a planar surface 1110 and is rectangular in shape. In alternate embodiments, the tray 1100 includes recesses having a cross section that corresponds with a shape of a surgical instrument. Further, in alternate embodiments, the tray 1100 comprises any suitable shaped configured to support surgical instruments thereon.

The tray comprises a front side 1115 and a rear side 1120. In the illustrated embodiment, the rear side 1120 tapers towards a center in order to provide additional open area to receive falling waste from the top of the birth delivery bed to a waste compartment therebeneath. In some embodiments, the tray 1100 comprises a disposable upper surface for easy cleaning. The tray is composed of any suitable, durable material, such as plastic.

In the illustrated embodiment, a lip 1130 is disposed around a perimeter of the tray 1100. The lip 1130 is configured to serve as a barrier to prevent objects from rolling or otherwise off of the tray 1100 during use. In some embodiments, the corners of the lip 1130 are rounded for safety and to provide more surface area. In the shown embodiment, the lip 1130 does not extend along the rear side 1120 of the tray 1100. This allows a physician to easily discard objects from the tray 1100 along the rear side 1120.

Figure 4:
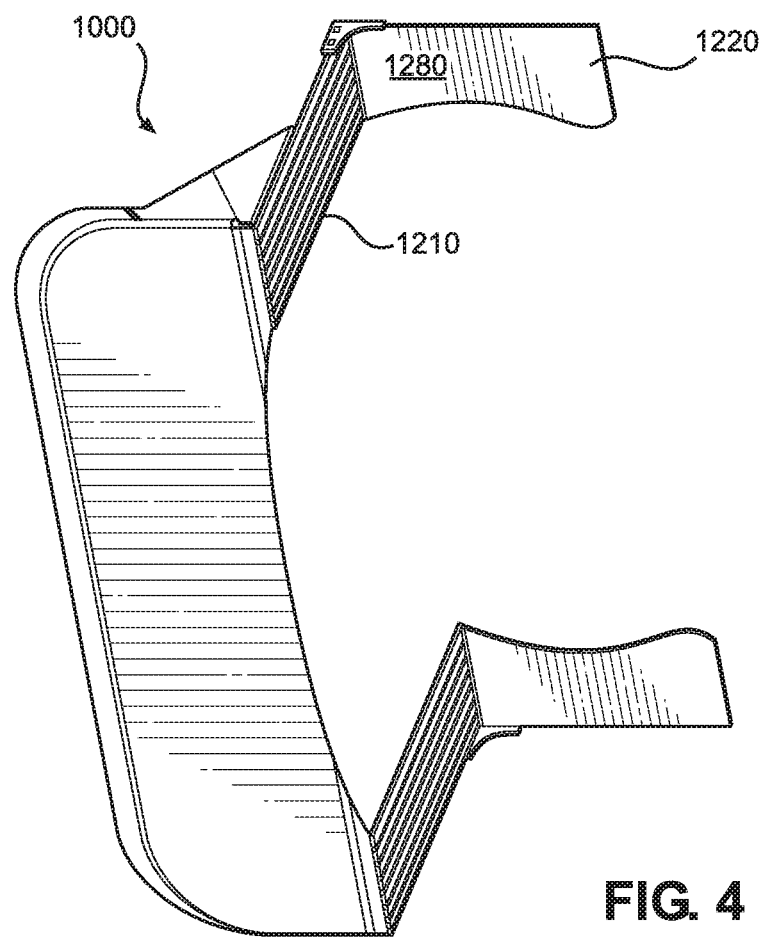
FIG. 4 shows a rear perspective view of an embodiment of the medical shelf.
Figure 5:
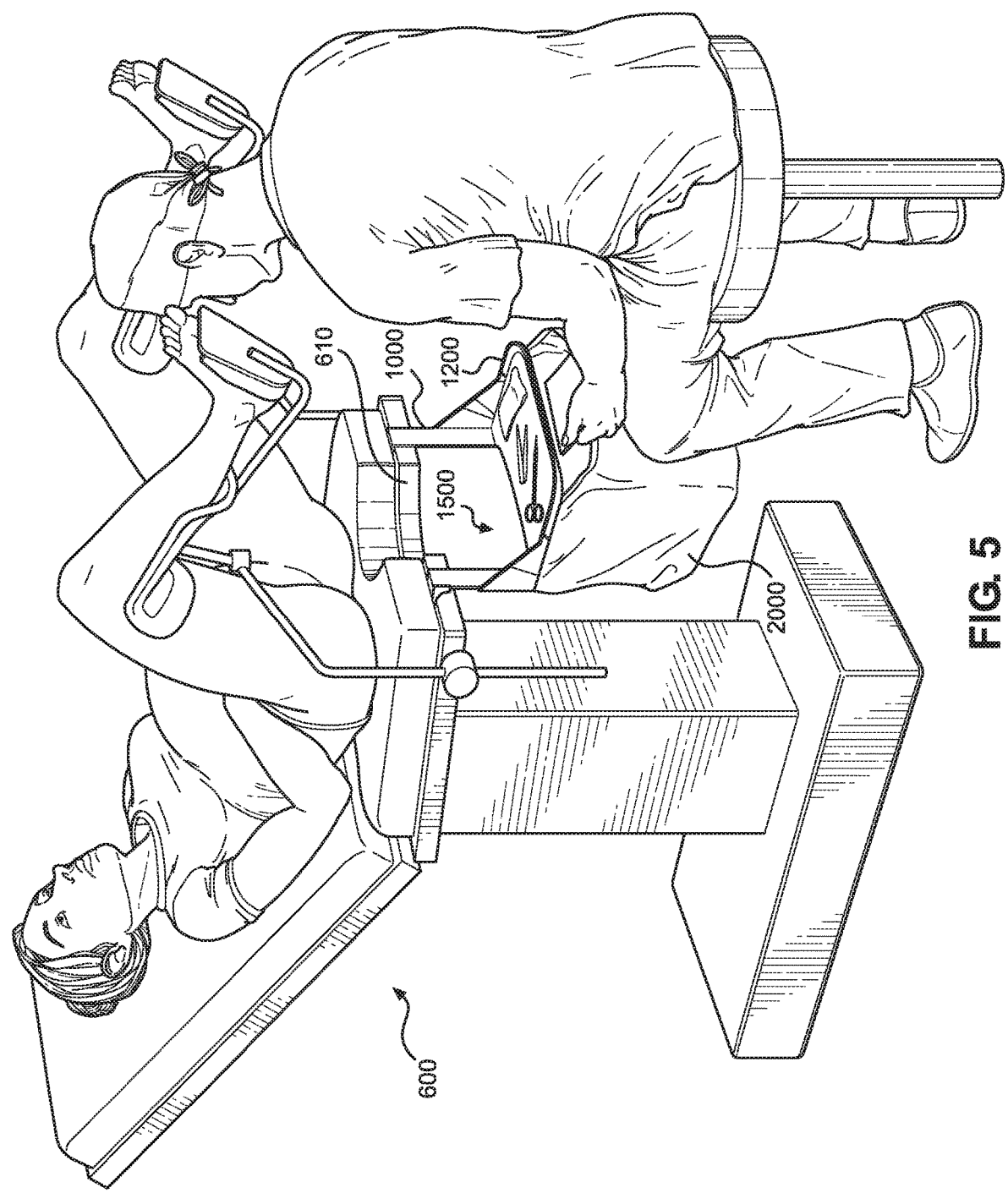
FIG. 5 shows a perspective view of an embodiment of the medical shelf secured to a birth delivery bed and in use.

A pair of arms 1200 extend from opposing ends of the rear side 1120 of the tray 1100, wherein the arms 1200 are configured to mount to an end of a birth delivery bed. In the illustrated embodiment, each arm 1200 comprises a first member 1210 and a second member 1220, forming an L-shaped configuration. In the illustrated embodiment, each member 1210, 1220 is planar and flat so as to reduce the potential interference of the arms during a procedure. In the illustrated embodiment, the first member 1210 extends perpendicularly from the tray 1100, wherein the second member 1220 extend perpendicularly from the uppermost end of the first member 1210. Moreover, the second member 1220 and the tray are disposed on opposing sides of the first member 1210 so as to form a Z-shaped cross-section. The first member 1210 comprises a uniform width, the width is measured as a distance between a pair of opposing edges 1225, 1230 thereof. However, in the shown embodiment, an interior side 1240 of the second member 1220 tapers towards a center thereof (as seen in FIG. 4, as well). In this way, the taper or curve of the interior side 1240 conforms to a curved central cutout of a birth delivery bed (as seen in FIG. 5).

In the illustrated embodiment, the medical shelf 1000 comprises a first brace 1300 and a second brace 1400, wherein the first brace 1300 is configured to stabilize and further secure each arm 1200 to the tray 1100 in a perpendicular position. The second brace 1400 is configured to secure each arm 1200 in the L-shaped configuration. Each brace comprises a tab 1320, 1420 having an aperture 1325 and a protrusion 1330, wherein the aperture 1325 is configured to receive the protrusion 1330 to form a friction fit therewith. In the illustrated embodiment, each brace comprises a pair of apertures and a pair of corresponding protrusions. In the shown embodiment, the tabs 1320, 1420 are triangular and have a tapered side 1340, wherein the tapered side 1340 tapers towards a center thereof.

The tab 1320 of the first brace 1300 extends from an exterior side 1225 of the first member 1210 and the protrusions 1330 extend from an edge of the tray 1100. Each tab 1320 of the first brace is pivotally secured to the first member to allow the apertures to selectively engage and disengage with the protrusions. The tab 1420 of the second brace 1400 extends from an exterior side 1225 of the second member 1220 and the protrusions 1330 extend from an edge of the exterior side 1225 of the first member. Each tab 1420 of the second brace 1400 is pivotally secured to second member 1220 to allow the apertures to selectively engage and disengage with the protrusions.

In some embodiments, when the apertures are disengaged with the protrusions and the tab is aligned in a same plane as the first member 1210 and second members, respectively, the arms are configured to fold in a stacked configuration with the tray for compact storage. In other embodiments, as shown in FIG. 2, the tab 1320 of the first brace 1300 comprises a fold 1345 so as to allow the tray to pivot or tilt upwards towards the arms 1200. The inclined function of the tray assists with the removal of waste from the surface 1110 after a procedure via the rear side 1120 thereof.

In the illustrated embodiment, the medical shelf 1000 is symmetrical about an axis disposed between the pair of arms. A gap 1500 is disposed between the pair of arms 1200. During a procedure the physician or other medical professional sits at the foot of the birth delivery bed and the patient is on the bed positioned at the foot of the bed. The gap 1500 allows the physician positioned on the front side of the tray 1100 to access the patient positioned on the rear side of the tray, as well as allowing any waste material to pass from the patient to a waste bag positioned beneath the medical shelf via the gap 1500. In the illustrated embodiment, the gap 1500 comprises the entire area between the pair of arms 1200.

Figure 3:
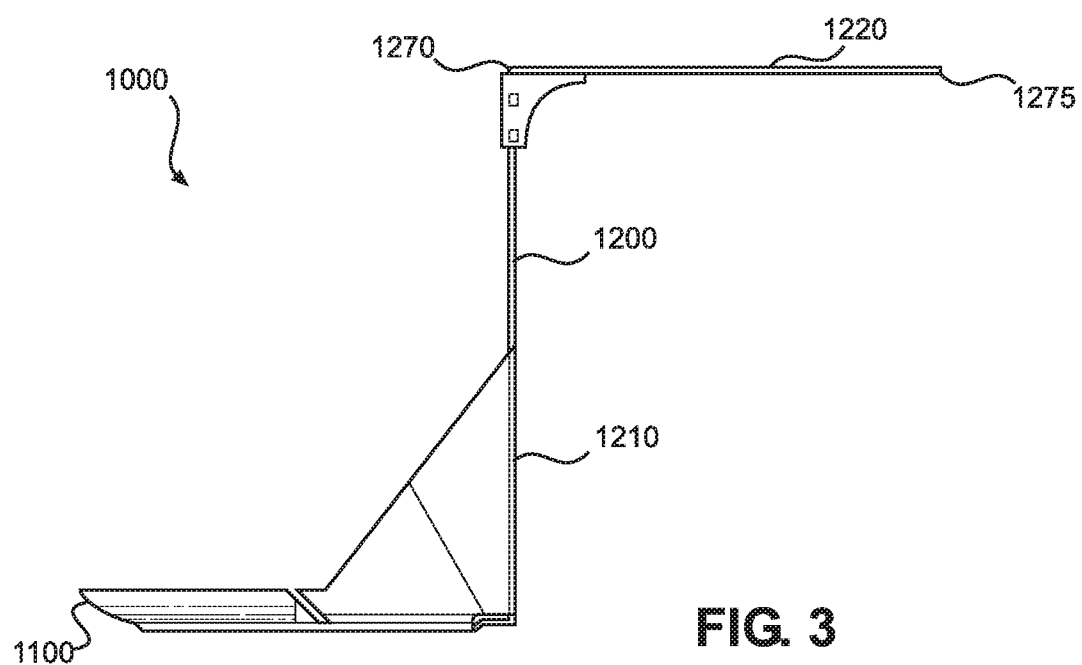
FIG. 3 shows a side view of an embodiment of the medical shelf.

Referring now to FIG. 3, there is shown a side view of an embodiment of the medical shelf. In the illustrated embodiment the first member 1210 comprises a length greater than the second member 1220. The length is measured between opposing ends 1270, 1275 of each of the respective members 1210, 1220. In some embodiments, the first member 1210 is telescopic to allow the physician to selectively adjust the height of the tray. In this way, a physician may comfortably access surgical instruments during a procedure according to the needs of the physician.

Referring now to FIG. 4, there is shown a rear perspective view of an embodiment of the medical shelf. The medical shelf 1000 is mountable to the birth delivery bed by securing the pair of arms to the deliver bed. In the illustrated embodiment, a lower surface 1280 of the second member 1220 comprises a fastener, such as an adhesive, to removably secure the medical shelf 1000 thereto. In alternate embodiments, any suitable fastener is used to removably secure the medical shelf to the birth delivery bed, such as clips or a bracket.

Referring now to FIG. 5, there is shown a perspective view of an embodiment of the medical shelf secured to a birth delivery bed and in use. In operation, the medical shelf 1000 is mounted to the birth delivery bed 600. The birth delivery bed 600 comprises a central semi-circular cutout 610 in order to allow the physician efficient access to the patient during a vaginal procedure. The medical shelf 1000 is designed to mount around the cutout 610 while preventing any obstruction of the physician performing the medical procedure on the patent. In the illustrated embodiment, the second members of the arms are slid between the surface of the table and the cushion of the birth delivery bed. In alternate embodiments, the second member 1220 is placed on the surface of the birth delivery bed and adhered thereto. In some embodiments, the medical shelf 1000 comprises a waste receptacle 2000 secured to the tray 1100 in order to conveniently receive waste during and after the procedure.

In a mounted position, the tray 1100 provides a surface that can receive surgical instruments to allow a medical professional the ability to access the instruments while performing a procedure on a patient positioned on the birth delivery bed. The medical shelf 1000 directly and easily secures to a birth delivery bed 600 with minimal securement required. This enables the physician to perform the procedure without having to turn his or her back to the patient, saving total procedure time and preventing loss of focus.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A medical shelf, comprising:
   a tray having a pair of arms extending from a rear side of the tray and forming a gap therebetween, wherein each arm comprises a first member secured to a second member;
   wherein the tray is configured to mount to an end of a birth delivery bed;
   wherein the medical shelf is configured to fold about a hinge formed between the tray and the first member, and to fold about a joint formed between the first member and the second member.

2. The medical shelf of claim 1, wherein the first member is perpendicular to the second member.

3. The medical shelf of claim 1, wherein the tray comprises a lip disposed around a perimeter thereof.

4. The medical shelf of claim 3, wherein the lip is disposed around all sides of the tray, except the rear side.

5. The medical shelf of claim 1, wherein the gap along an entire distance between an interior side of the pair of arms.

6. The medical shelf of claim 1, further comprising a first brace extending from a first end of each of the arms and configured to removably secure to the tray, wherein the first brace fixes an angle formed between the arm and the tray.

7. The medical shelf of claim 6, wherein the first brace comprises:
   a tab having an aperture, wherein the tab extends from an edge of the first member;
   a protrusion extending from an edge of the tray;
   such that the aperture is configured to align with and secure to the protrusion when the first member is perpendicular to the tray, thereby forming a locked position.

8. The medical shelf of claim 7, wherein the tab is pivotally secured to the first member.

9. The medical shelf of claim 6, further comprising a second brace extends between the first member and the second member.

10. The medical shelf of claim 9, wherein the second brace comprises:
    a tab having an aperture, wherein the tab extends from an edge of the second member;
    a protrusion extending from an edge of the first member;
    such that the aperture is configured to align with and secure to the protrusion when the first member is perpendicular to the second member.

11. The medical shelf of claim 10, wherein the tab is pivotally secured to the first member.

12. The medical shelf of claim 1, wherein the second member is configured to removably secure to the birth deliver bed.

13. The medical shelf of claim 12, wherein the second member comprises an adhesive adapted to secure to the birth delivery bed.

14. The medical shelf of claim 1, wherein the first member comprises a length greater than the second member.

15. The medical shelf of claim 1, wherein a length of the gap is equal to or greater than a distance of a central cutout at an edge of the birth delivery bed.

16. The medical shelf of claim 1, wherein an interior side of the second member tapers towards a center thereof.

17. The medical shelf of claim 1, further comprising a waste receptacle secured to the tray.

18. A medical shelf, comprising:
    a tray having a pair of arms extending from a rear side of the tray and forming a gap therebetween, wherein each arm comprises a first member secured to a second member;
    wherein the tray is configured to mount to an end of a birth delivery bed;
    a first brace extending from a first end of each of the arms and configured to removably secure to the tray, wherein the first brace fixes an angle formed between the arm and the tray;
    wherein the first brace comprises:
       a tab having an aperture, wherein the tab extends from an edge of the first member;
       a protrusion extending from an edge of the tray;
       such that the aperture is configured to align with and secure to the protrusion when the first member is perpendicular to the tray, thereby forming a locked position.

19. A medical shelf, comprising:
    a first arm and a second arm extending from a rear side of a tray, wherein the first arm and the second arm each comprises a first member secured to a second member;
    wherein the first member is pivotally affixed to the tray and the second member is pivotally affixed to the first member, such that the tray, the first member, and the second member form a Z-shaped cross-section;
    wherein a gap is defined by the rear side of the tray and an interior side of each arm;
    wherein the tray comprises a planar upper side configured support surgical instruments thereon and a lip extending about the perimeter excluding the gap;
    wherein a mounted position the second member is secured to a birth deliver bed such that the tray is disposed lower the birth delivery bed and the support surgical instruments are accessible.

* * * * *